United States Patent [19]

Bringhurst et al.

[11] Patent Number: Plant 6,580

[45] Date of Patent: Jan. 31, 1989

[54] STRAWBERRY PLANT

[75] Inventors: Royce S. Bringhurst, Davis; Victor Voth, Santa Ana, both of Calif.

[73] Assignee: Regents of the University of California, Berkeley, Calif.

[21] Appl. No.: 75,915

[22] Filed: Jul. 16, 1987

[51] Int. Cl.[4] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A strong day-neutral type with exceptionally symmetrical conic fruit of fine flavor; resistant to Verticillium Wilt and capable of fruiting about three months after planting under satisfactory growing conditions regardless of planting time. The plant is of interest in all situations where 'Fern' or 'Hecker' are grown.

2 Drawing Sheets

DESCRIPTION

This invention relates to a new and distinctive day-neutral type strawberry cultivar designated as 'Yolo' which is the result of a cross between 'Hecker' (U.S. Plant Pat. No. 4,507) and Cal 71.98-605 (not patented) made in 1975. The pedigree is as follows:

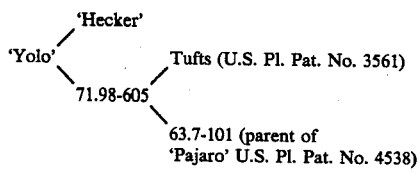

'Yolo' has been propagated asexually by runners and has been tested at various University of California field stations and research facilities and to a limited extent in a few growers' fields under Test Agreement.

In the photographs:

Figure 1:
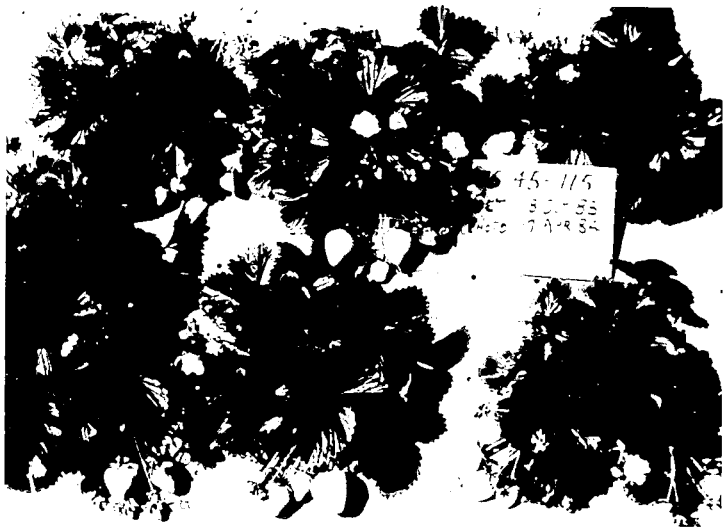
FIG. 1 shows typical growth, flowering and fruiting characteristics of the plant.
Figure 2:
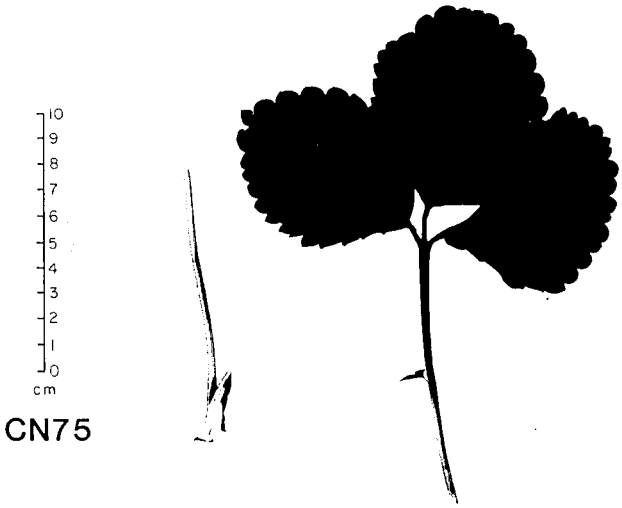
FIG. 2 shows a typical midsummer mature leaf from a plant in full fruit.
Figure 3:
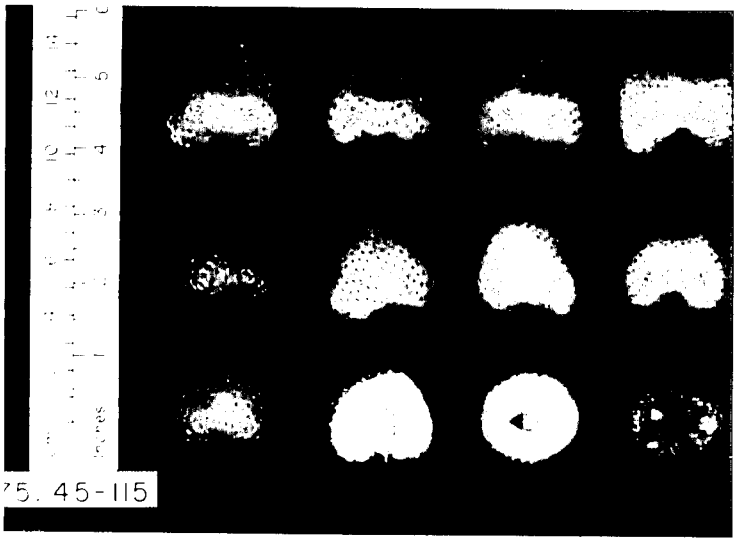
FIG. 3 shows representative early-season fruit with longitudinal and cross-sectional views.

'Yolo' commences fruiting about three months after planting, whether fresh dug or cold storage plants are used, regardless of planting time provided that satisfactory growing conditions prevail. 'Yolo' is strongly day-neutral similar to 'Hecker', 'Brighton' and 'Fern' (U.S. Plant Pat. No. 5,267).

Plants and foliage: 'Yolo' plants are more compact in growing habit than those of 'Selva'. Leaf color and characteristics from late summer nursery plants are compared with those of 'Selva', 'Fern' and 'Hecker' in Table 1.

TABLE 1

| | YOLO | SELVA | FERN | HECKER |
|---|---|---|---|---|
| Color | 2.5GY4/3 | 7.5GY4/4 | 7.5GY4/4 | 2.5GY4/3 |
| Shape (length/width) | 1.16 | 1.20 | 1.10 | 1.13 |
| Base angle of terminal leaflet | 53° | 51° | 58° | 56° |
| Size of terminal | 72 | 86 | 70 | 76 |

TABLE 1-continued

| | YOLO | SELVA | FERN | HECKER |
|---|---|---|---|---|
| leaflets | | | | |
| Serrations of terminal leaflets | 8.8 | 9.8 | 9.3 | 8.0 |
| Petiolule length (MM) | 9.5 | 11.4 | 7.7 | 9.3 |
| Petiole length (MM) | 159 | 161 | 155 | 137 |
| Bract leaflet position | 75 | 68 | 61 | 64 |

As shown above 'Yolo' leaves are about the same color as those of 'Hecker', darker and less yellow than those of 'Selva' or 'Fern' (Munsell Color System—Nickerson Color Fan). Terminal leaflets are somewhat elongated, similar to those of 'Hecker', less elongated than those of 'Selva' as shown by the length/width measurements. 'Yolo' terminal leaflets are about the same size as those of 'Fern' or 'Hecker', smaller than those of 'Selva' as shown by extracting the square root of the length × width measurement. Half terminal leaflet serrations number less on 'Yolo' than on 'Fern' or 'Selva' but more than on 'Hecker'. Petiolules (terminal leaflet stems) of 'Yolo' are about the same length as those of 'Hecker', shorter than 'Selva' and longer than 'Fern'. 'Yolo' plants are about the same size as those of 'Selva' or 'Fern' but larger than those of 'Hecker' as estimated by petiole length. Bract leaflets occur on about one-third of the leaf petioles of 'Yolo' and they tend to be higher up on 'Yolo' (about 75%) than on the comparison cultivars. Runner production in nursery plants of 'Yolo' is good, about equal to that of 'Hecker' and 'Fern' but a bit less than 'Selva'.

Isozymes in leaf extracts: 'Yolo' has been characterized for three enzyme systems by starch gel electrophoresis: A. Phosphoglucoisomerase (PG1); B. Leucine Amino Peptidase (LAP); and C. Phosglucomutase (PGM). They compared with other day-neutral California cultivars as follows:

TABLE 2

| | YOLO | SELVA | FERN | HECKER | APTOS & BRIGHTON |
|---|---|---|---|---|---|
| PGI | A1 | A2 | A4 | A1 | A4 |
| LAP | B1 | B3 | B3 | B1 | B3 |
| PGM | C2 | C2 | C2 | C4 | C4 |

For the procedure see: J. Amer. Soc. HortSci. 106:684–1981. 'Yolo' can thus be distinguished unambiguously from any of other California day-neutral California cultivars by using the 3 enzyme systems.

Disease and pest reaction: 'Yolo' is highly resistant to (tolerant of) the virus diseases common in California including "Mild Yellow Edge" alone and in complexes. 'Yolo' is resistant to Verticillum wilt (about equal to 'Hecker'); moderately susceptible to common leaf spot (Ramularia), similar to 'Selva' and relatively sensitive to infestation by two-spotted mites.

Flowering, fruiting, fruit and production characteristics: 'Yolo' is a strong day-neutral similar to 'Fern' or 'Hecker', capable of flowering and fruiting anytime, effectively independent of day-length. Flowers are borne on medium long peduncles, similar to 'Selva'. The flowers are completely self-fertile with ample pollen throughout the season and pollination is excellent with few malformed fruit. The fruit of 'Yolo' is very symmetrical short conic in shape with occasional wedge. The centers may be somewhat hollow. 'Yolo' yield and midseason fruit and quality characteristics are compared with those of 'Selva', 'Fern' and 'Hecker' as grown under optimum conditions under the "hill" system in winter plantings at the University of California Strawberry Research Facility, Watsonville in Table 3 as follows:

TABLE 3

| | YOLO | SELVA | FERN | HECKER |
|---|---|---|---|---|
| Yield (Gr/plant) | 1180 | 1557 | 1502 | 1556 |
| Size (Gr/fruit) | 22.0 | 25.9 | 22.4 | 16.2 |
| Firmness | 5.8 | 6.8 | 5.4 | 5.3 |

TABLE 3-continued

| | YOLO | SELVA | FERN | HECKER |
|---|---|---|---|---|
| Color | 7R4/11 | 7R4/11 | 5R3.5/12 | 7.5R4.5/13 |
| Ascorbic acid | 36.0 | 24.1 | 27.8 | 46.7 |
| Soluble solids | 9.1 | 8.1 | 7.9 | 7.6 |

'Yolo' is capable of yielding almost as much as the high yielding day-neutral cultivars. Fruit size averages about the same size as that of 'Fern', larger than that of 'Hecker' and smaller than that of 'Selva'. 'Yolo' fruit is firmer than that of 'Fern' or 'Hecker' but not as firm as that of 'Selva' as measured by a penetrometer equipped with a "Hunter Force Gage". The fruit skin color is about the same as that of 'Selva', less red than that of 'Fern' (ibid). The finish is exceptionally bright and attractive. The flesh is about the same color as the skin with a lighter ring around the core. The achenes are bright yellow, positioned about even with the skin surface. The calyx is medium to small sized positioned about even with the base of the fruit. 'Yolo' fruit averages higher in ascorbic acid than 'Selva' and 'Fern' but somewhat lower than 'Hecker' as measured by the Loeffler and Ponting method (1942, J. Indust. and Engin. Chem. 14:846). 'Yolo' tends to be higher in soluble solids than the three comparson cultivars. The flavor of 'Yolo' is exceptionally good, comparing favorably with that of 'Fern'. 'Yolo' is recommended for fresh market and processing, for commercial planting and home gardening, particularly where "off season" fruiting is desired.

We claim:

1. The new distinct variety of strawberry plant herein described and illustrated and identified by the characteristics enumerated above together with the parts thereof.

* * * * *